US00PP25908P3

(12) United States Plant Patent
Olesen

(10) Patent No.: US PP25,908 P3
(45) Date of Patent: Sep. 22, 2015

(54) CLIMBING ROSE PLANT NAMED 'POULCY023'

(50) Latin Name: ***Rosa* hybrid**
Varietal Denomination: Poulcy023

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 168 days.

(21) Appl. No.: 13/986,918

(22) Filed: Jun. 14, 2013

(65) Prior Publication Data

US 2014/0373203 P1 Dec. 18, 2014

(51) Int. Cl.
*A01H 5/02* (2006.01)

(52) U.S. Cl.
USPC ..... Plt./113

(58) Field of Classification Search
USPC ..... Plt./101, 109, 113
See application file for complete search history.

(56) References Cited

PUBLICATIONS

UPOV-PLUTO Plant Variety Database, International Union for Protection of New Varieties of Plants, Jan. 19, 2015, obtained for cultiver 'Poulcy023' (1 page total).*
Poulsen Roser A/S catalog; Retrieved from the Internet http://www.poulsenroser.com (1 page total).*
"Catalogorosales" Retrieved from the Internet http://www.viverosguzman.es/contenido/descargas/rosales.pdf (10 pages total).*

* cited by examiner

*Primary Examiner* — Susan McCormick Ewoldt

(57) ABSTRACT

A new garden rose plant of the Climbing class which has abundant, salmon pink flowers and attractive foliage. This new and distinct variety has shown to be uniform and stable in the resulting generations from asexual propagation.

1 Drawing Sheet

Botanical designation: *Rosa* hybrid.
Variety denomination: 'Poulcy023'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2003 and the resulting seeds were planted in a controlled environment in Fredensborg, Denmark. The new variety, named 'Poulcy023', originated as a single seedling from the stated cross.

The new variety may be distinguished from its male pollen parent and female seed parent primarily by flower coloration. The female seed parent has red flowers. The male pollen parent has medium red flowers. The claimed variety has salmon pink flowers.

The objective of the hybridization of this rose variety was to create a new and distinct variety for garden use with unique qualities, such as:

1. Uniform and abundant salmon pink flowers;
2. Vigorous, but compact growth when propagated both as a budded rose and on its own roots;
3. Exceptional disease resistance; and
4. Reduced apical dominance in flowering habit. The new variety consistently produces flowers evenly from the lower branches to the top of the plant.

This combination of qualities is not present in previously available commercial cultivars of this type, known to the inventor, and distinguish 'Poulcy023' from all other varieties of which we are aware.

As part of the rose development program, Mogens N. Olesen germinated the seeds from the aforementioned hybridization during winter of 2003 and conducted evaluations on the resulting seedlings in a controlled environment in Fredensborg, Denmark. 'Poulcy023' was selected in the spring of 2004 by the inventor as a single plant from the progeny of the aforementioned hybridization.

Asexual reproduction of 'Poulcy023' by traditional budding and rooted cuttings was first done by Mogens N. Olesen in the nursery in Fredensborg, Denmark in July, 2004. This initial and other subsequent asexual propagations conducted in controlled environments have demonstrated that the characteristics of 'Poulcy023' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulcy023'.

Specifically illustrated in the drawing are flowers at various stages of development, flower in parts, leaves, and stems. Plants shown in the illustration are 2 years of age.

DETAILED DESCRIPTION OF THE VARIETY

The following is a description of 'Poulcy023', as observed in its growth in in a field nursery in Marion County, Oreg.

Observed plants are 3 years of age, and were grown on their own roots. Color references are made using The Royal Horticultural Society (London, England) Colour Chart, 2001, except where common terms of color are used.

For a comparison, several physical characteristics of the rose variety 'Poulyc007', U.S. Plant Pat. No. 15,482 are compared to 'Poulcy023' in Chart 1.

CHART 1

| | 'Poulcy023' | 'Poulyc007' |
|---|---|---|
| Petal Count | 35 petals total, 5 of which are petaloids | 50 to 55 petals |
| Flower Diameter | 50 mm | 75 mm |
| General Tonality of Flower Color | Red Group 52B | Red Group 55D |

Flower and Flower Bud

Blooming habit: Continuous.

Flower bud:

*Size.*—Upon opening, 20 mm in length from base of receptacle to end of bud. Bud diameter is 12 mm.

*Bud form.*—Urceolate.

*Bud color.*—As sepals divide petals are Red Group 52B.

*Sepal inner surface.*—Color: Yellow-Green Group 146C with moderate intonations of Greyed-Red Group 181B. Surface: Smooth, moderately pubescent.

*Sepal outer surface.*—Color: Yellow-Green Group 144A with strong intonations of Greyed-Purple Group 183A. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—16 mm long by 7 mm wide.

*Receptacle.*—Texture: Smooth. Size: 8 mm in height by 7 mm wide. Color: Yellow-Green Group 144A. Strong anthocyanic pigments the color of Greyed-Purple Group 183A observed. Shape: Elliptical.

*Pedicel.*—Surface: Somewhat rough, with stipitate glands. Length: 15 to 25 mm. Diameter: 2.5 mm on average. Color: Yellow-Green Group 144B. Strong anthocyanic pigments the color of Greyed-Purple Group 184A observed. Strength: Moderate.

*Peduncle.*—Length: 5 to 30 cm. Diameter: 3 to 5 mm. Color: Yellow-Green Group 144A with strong intonations of Greyed-Purple Group 184A.

Flower bud development: Flower buds are borne in panicle like clusters of 3 to 13 flower buds on each peduncle. Reduced apical dominance in flower habit causes flower buds develop evenly from the base of the plant to the upper branches.

Flower bloom:

*Fragrance.*—Light.

*Duration.*—The blooms have a duration on the plant of approximately 7 to 10 days. Petals fall cleanly away from plant after flowers have fully matured.

*Size.*—Flower diameter is 50 mm when open. Flower depth is 22 mm.

*Flower shape.*—General shape is a open cup with petals that curve out from the center.

*Shape of flower, side view.*—The upper portion is a flattened convex. Lower portion is concave.

Petalage: Under normal conditions, flowers have 35 petals total, 5 of which are petaloids.

General tonality of flower: Open flowers are Red Group 52B. Tonality changes to Red-Purple Group 62A as the flower ages.

Petal color:

*Upon opening, outer and inner petals.*—Upper surface: Red Group 52B. Lower surface: Red-Purple Group 58C splashed with intonations of Red-Purple Group 62C at the petal base.

*Basal petal spots, upon opening.*—Upper surface: Yellow Group 4C. Lower surface: Yellow Group 4D.

*After opening, outer and inner petals.*—Upper surface: Red-Purple Group 58C. Lower surface: Red-Purple Group 61D splashed with Red-Purple Group 62D.

*Basal petal spots, after opening.*—Upper surface: Yellow Group 8D. Lower surface: Yellow Group 8D.

Petals:

*Petal reflex.*—Light to none.

*Margin.*—Entire with a point at the center. Moderate to strong undulations of margin observed.

*Shape.*—Narrow elliptic. Apex shape: Cuspidate. Base shape: Acute.

*Size.*—30 mm (l) 30 mm (w).

*Texture.*—Smooth.

*Thickness.*—Average.

Petaloids:

*Size.*—15 mm (l) by 11 mm (w).

*Quantity.*—5 on average.

*Shape.*—Elliptical, with a cleft at the apex. Base is acute. Apex is rounded.

*Color.*—Upper surface is Red Group 52B. The lower surface is Red-Purple Group 58C splashed with intonations of Red-Purple Group 62C at the petal base. Basal petaloid spots are Yellow Group 4C.

Reproductive organs:

*Pollen.*—None observed.

*Anthers.*—Size: 2 mm in length. Color: Greyed-Orange Group 163B. Quantity: 35 on average.

*Filaments.*—Color: Yellow Group 4B. Length: 8 mm.

*Pistils.*—Length: 3 mm. Quantity: 15 on average.

*Stigmas.*—Color: Yellow-Green Group 154D.

*Styles.*—Color: Yellow-Green Group 154D.

*Location of stigmas.*—Inferior in location relative to the length of the filaments and the height of the anthers.

*Hips.*—None Observed.

Plant

Plant growth: Arching. Plants are 100 cm in height, and 90 cm wide.

Stems:

*Color.*—Juvenile growth: Yellow-Green Group 146B with intonations of Greyed-Purple Group 183B. Mature growth: Yellow-Green Group 146C.

*Length.*—On average, canes are 60 cm from the base of the plant to the flowering portion.

*Diameter.*—9 mm.

*Internodes.*—On mature canes, there is an average distance of 50 mm between nodes.

*Surface texture.*—Young wood: Smooth. Older wood: Generally smooth. Some small prickles appear at base of stem.

Long prickles:

*Incidence.*—4 prickles per 10 cm of stem.

*Size.*—Average length of prickles on mature stems is 5 mm.

*Shape.*—Upper portion is concave. Lower portion is concave.

*Color.*—Juvenile prickles: Greyed-Red Group 180A. Mature prickles: Greyed-Red Group 181C.

Plant foliage:

*Compound leaf.*—155 mm (l)×90 (w).

*Quantity.*—2 leaves per 10 cm of stem on average.

*Leaf bearing angle to the stem.*—45 degrees.

*Color of juvenile foliage.*—Upper side: Yellow-Green Group 144A. Rachis: Strong intonations of Greyed-Red Group 181A on the upper surface. Lower side: Yellow-Green Group 146B.

*Color of mature foliage.*—Upper side: Yellow-Green Group 147A. Lower side: Yellow-Green Group 147B.

Plant leaves and leaflets:

*Stipules.*—Size: 22 mm in length. Quantity: 2 per compound leaf. Shape: Linear, slightly broad based with outward extending apecies. Margins: Shallow serrations. Color: Yellow-Green Group 144A.

*Petiole.*—Length: 25 to 45 mm. Diameter: 2 mm.

*Upper surface.*—Color: Yellow-Green Group 144A.

*Lower surface.*—Color: Yellow-Green Group 144A. Observations: Small prickles observed.

*Rachis.*—Length: 55 to 60 mm. Upper surface: Color: Yellow-Green Group 144A.

*Lower surface.*—Color: Yellow-Green Group 144A. Observations: Small prickles observed.

*Leaflet.*—Quantity: Normal number of leaflets leaves in middle of the stem is 5 leaflets. Margins: Serrated. Size: Average size of the terminal leaflet on normal leaves is 50 mm in length by 35 mm wide. Shape: Generally elliptical. Base: Rounded. Apex: Mucronate. Texture: Smooth. Thickness: Average. Arrangement: Odd pinnate. Venation: Reticulate. Glossiness: Glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Climbing rose class named 'Poulcy023', substantially as illustrated and described herein, due to its abundant salmon pink flowers, disease resistance, and extended period of bloom.

* * * * *

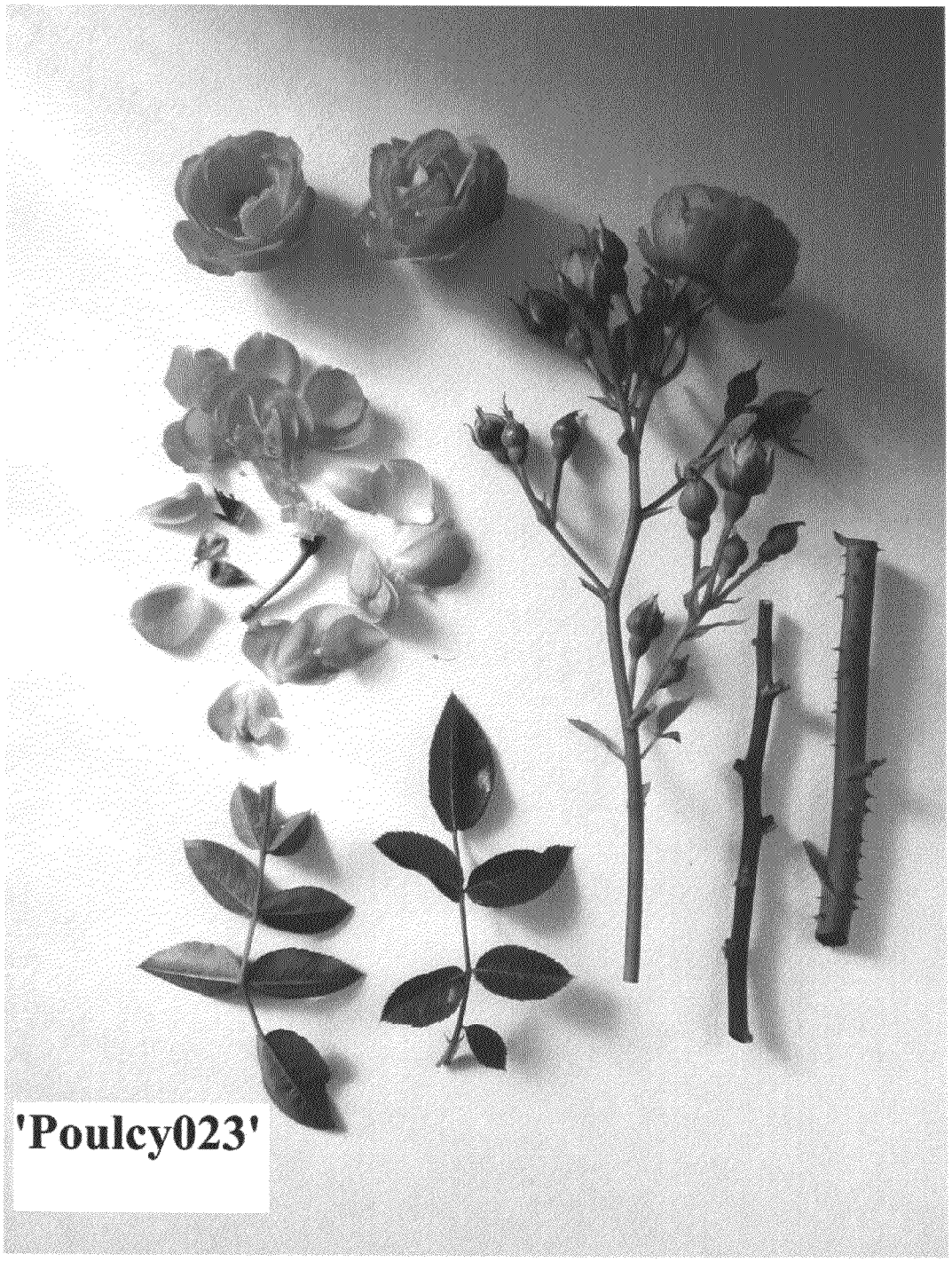
'Poulcy023'